(12) United States Patent
Pellizzer et al.

(10) Patent No.: US 8,945,403 B2
(45) Date of Patent: Feb. 3, 2015

(54) MATERIAL TEST STRUCTURE

(75) Inventors: Fabio Pellizzer, Cornate D'adda (IT); Innocenzo Tortorelli, Moncalieri (IT); Christina Papagianni, San Jose, CA (US); Gianpaolo Spadini, Scotts Valley, CA (US); Jong Won Lee, San Francisco, CA (US)

(73) Assignee: Micron Technology, Inc., Boise, ID (US)

( * ) Notice: Subject to any disclaimer, the term of this patent is extended or adjusted under 35 U.S.C. 154(b) by 338 days.

(21) Appl. No.: 13/458,048

(22) Filed: Apr. 27, 2012

(65) Prior Publication Data

US 2013/0283936 A1    Oct. 31, 2013

(51) Int. Cl.
*H01B 13/00* (2006.01)
(52) U.S. Cl.
USPC ............... 216/13; 216/37; 216/67; 438/689; 438/690; 438/692
(58) Field of Classification Search
USPC ............... 216/13, 37, 67; 438/689–692
See application file for complete search history.

(56) References Cited

U.S. PATENT DOCUMENTS

| | | | |
|---|---|---|---|
| 6,048,802 A * | 4/2000 | Avanzino et al. | 438/763 |
| 6,271,143 B1 | 8/2001 | Mendicino | |
| 6,576,546 B2 | 6/2003 | Gilbert et al. | |
| 6,600,333 B1 * | 7/2003 | Martin et al. | 324/750.3 |
| 6,635,528 B2 | 10/2003 | Gilbert et al. | |
| 6,773,930 B2 | 8/2004 | Summerfelt et al. | |
| 7,741,636 B2 | 6/2010 | Ho | |
| 7,787,352 B2 | 8/2010 | Bar-Sadeh et al. | |
| 2006/0014376 A1 * | 1/2006 | Agarwala et al. | 438/622 |
| 2010/0279484 A1 * | 11/2010 | Wang et al. | 438/396 |

* cited by examiner

*Primary Examiner* — Lan Vinh
*Assistant Examiner* — Maki Angadi
(74) *Attorney, Agent, or Firm* — Brooks, Cameron & Huebsch, PLLC

(57) ABSTRACT

Material test structures having cantilever portions and methods of forming the same are described herein. As an example, a method of forming a material test structure includes forming a number of electrode portions in a first dielectric material, forming a second dielectric material on the first dielectric material, wherein the second dielectric material includes a first cantilever portion and a second cantilever portion, and forming a test material on the number of electrode portions, the first dielectric material, and the second dielectric material.

17 Claims, 12 Drawing Sheets

_US 8,945,403 B2_

MATERIAL TEST STRUCTURE

TECHNICAL FIELD

The present disclosure relates generally to material test structures and methods, and more particularly to material test structures having cantilever portions.

BACKGROUND

Memory devices are utilized as non-volatile memory for a wide range of electronic applications in need of high memory densities, high reliability, and data retention without power. Memory devices are typically provided as internal, semiconductor, integrated circuits in computers or other electronic devices. There are many different types of memory, including random-access memory (RAM), read only memory (ROM), dynamic random access memory (DRAM), synchronous dynamic random access memory (SDRAM), flash memory, and resistive memory, among others. Types of resistive memory include phase change random access memory (PCRAM) and resistive random access memory (RRAM), for instance.

Various memory cells, such as resistive memory cells include a resistive storage element whose resistance can be adjusted to represent a number of different data states. For instance, voltage and/or current pulses can be applied to such resistive memory cells to program the resistive storage element to a particular resistance level corresponding to a particular data state, and the particular data state of the cell can be read by determining the resistance level of the resistive storage element, e.g., by sensing a current through the cell responsive to an applied voltage.

As an example, resistive storage elements can include a resistance variable material, such as a phase change material or metal oxide, formed between a pair of electrodes. The properties of a resistance variable material can affect the characteristics of a memory cell comprising the particular resistance variable material. As such, it can be useful to test the properties, e.g., physical and/or electrical properties, of different memory cell materials and/or alloys thereof. However, testing various different memory cell materials without contaminating production tools and/or the memory cell materials themselves can be challenging. In addition, fabrication of test structures used to test different memory cell materials can be time consuming and process intensive.

DETAILED DESCRIPTION

Figure 1A:
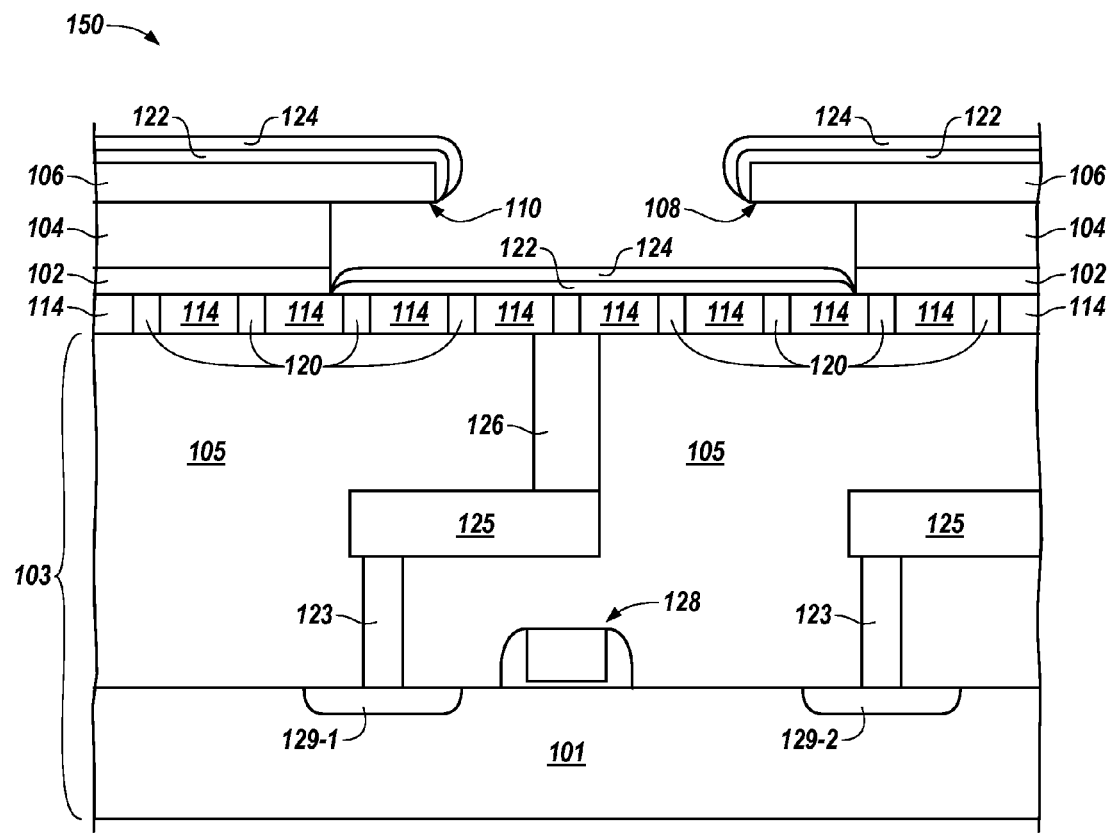
FIGS. 1A-1B illustrate cross-sectional views of material test structures in accordance a number of embodiments of the present disclosure.

Material test structures having cantilever portions and methods of forming the same are described herein. As an example, a method of forming a material test structure includes forming a number of electrode portions in a first dielectric material, forming a second dielectric material on the first dielectric material, wherein the second dielectric material includes a first cantilever portion and a second cantilever portion, and forming a test material on the number of electrode portions, the first dielectric material, and the second dielectric material.

Embodiments of the present disclosure can provide material test structures that are isolated, e.g., electrically, from adjacent material test structures. Embodiments of the present disclosure can also include forming the test material on electrodes, which are not affected by further processing after the formation and planarization of the electrodes.

In the following detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and/or structural changes may be made without departing from the scope of the present disclosure.

The figures herein follow a numbering convention in which the first digit or digits correspond to the drawing figure number and the remaining digits identify an element or component in the drawing. Similar elements or components between different figures may be identified by the use of similar digits. For example, 112 may reference element "12" in FIG. 1, and a similar element may be referenced as 212 in FIG. 2D. Also, as used herein, "a number of" a particular element and/or feature can refer to one or more of such elements and/or features.

Figure 1B:
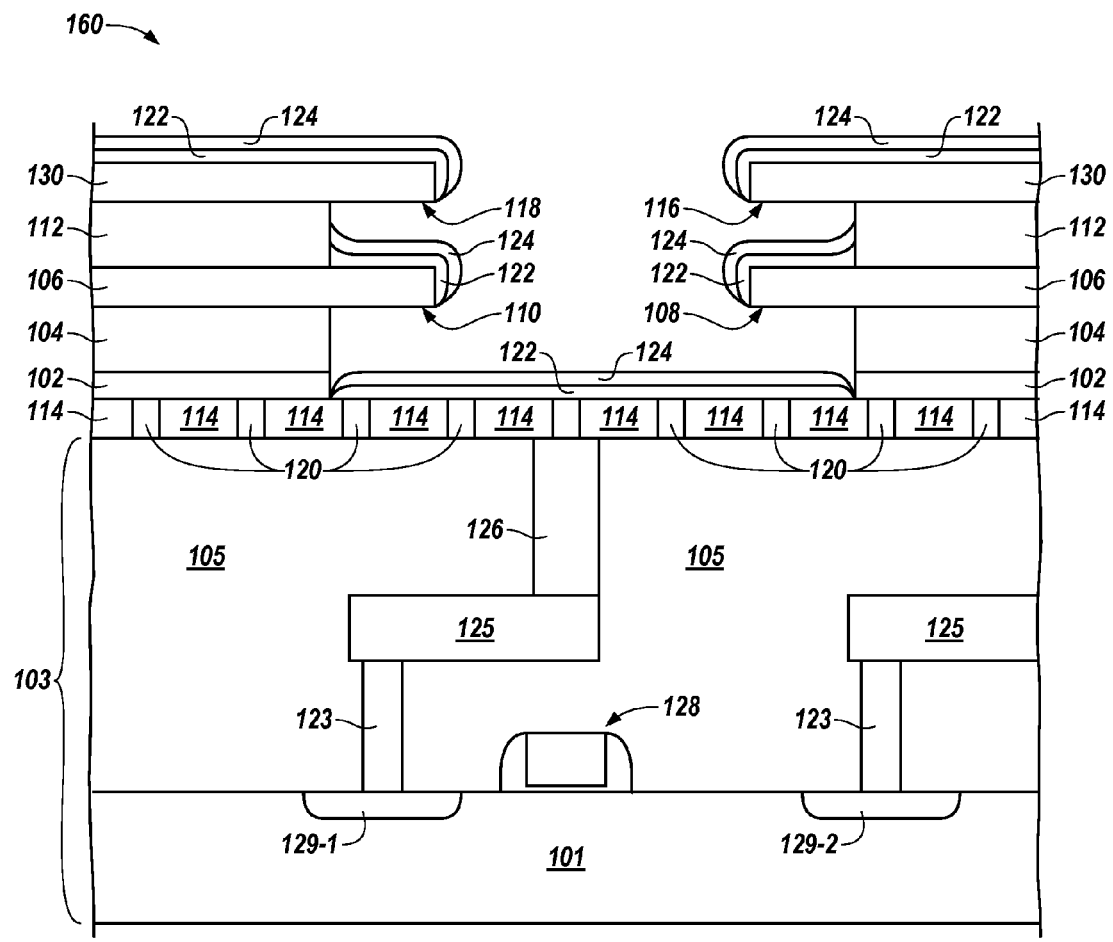

FIGS. 1A-1B illustrate cross-sectional views of material test structures in accordance a number of embodiments of the present disclosure. FIG. 1A illustrates a cross-sectional view of a material test structure 150 having one level of cantilever portions in accordance with a number of embodiments of the present disclosure. In one or more embodiments, material test structures can include a number of levels of cantilever portions. The material test structure 150 includes a test material 122 whose properties, e.g., physical and/or electrical characteristics, can be tested and observed using the material test structure of the present disclosure. The material test structure 150 can be used to simulate operation of a memory cell during the testing of different test materials. The test material 122 can be, for example, a resistance variable material, e.g., a phase change material. The test material can be a chalcogenide, e.g., a Ge—Sb—Te (GST) material such as $Ge_2Sb_2Te_5$, $Ge_1Sb_2Te_4$, $Ge_1Sb_4Te_7$, etc., among other resistance variable materials. The hyphenated chemical composition notation, as used herein, indicates the elements included in a particular mixture or compound, and is intended to represent all stoichiometries involving the indicated elements. Other resistance variable materials can include Ge—Te, In—Se, Sb—Te, Ga—Sb, In—Sb, As—Te, Al—Te, Ge—Sb—Te, Te—Ge—As, In—Sb—Te, Te—Sn—Se, Ge—Se—Ga, Bi—Se—Sb, Ga—Se—Te, Sn—Sb—Te, In—Sb—Ge, Te—Ge—Sb—S, Te—Ge—Sn—O, Te—Ge—Sn—Au, Pd—Te—Ge—Sn, In—Se—Ti—Co, Ge—Sb—Te—Pd, Ge—Sb—Te—Co, Sb—Te—Bi—Se, Ag—In—Sb—Te, Ge—Sb—Se—Te, Ge—Sn—Sb—Te, Ge—Te—Sn—Ni, Ge—Te—Sn—Pd, and Ge—Te—Sn—Pt, for example. Other examples of resistance variable materials include transition metal oxide materials or alloys including two or more metals, e.g., transition metals, alkaline earth metals, and/or rare earth metals. Embodiments are not limited to a particular resistance variable material or materials. For instance, other examples of resistance variable materials that can be used as test materials on the test material structure include binary metal oxide materials, colossal magnetoresistive materials, and/or various polymer based resistance variable materials, among others.

The material test structure illustrated in FIG. 1A includes portions of the test material 122 and the electrode material 124 formed on cantilever portions 108 and 110. The electrode material 124 can act as a top electrode for the material test structure. In a number of embodiments, the electrode material 124 can be AlCu, Cu, Ta, TaN, TiN, TiAlN, Pt, Ti, $TiO_x$, $InSnO_x$, $YBa_2Cu_3O_{7-x}$, among other materials. The portion of the test material 122 and the electrode material 124 formed on electrodes 120 is noncontiguous with the portion of the test material 122 and the electrode material 124 formed on cantilever portions 108 and 110, which provides for the test material 122 and electrode material 124 formed on the electrodes 120 to be separate from the test material and electrode material of adjacent material test structures to avoid electrical shorts between adjacent test structures. The test material 122 and electrode material 124 can be formed using a non-conformal deposition process to form the noncontiguous portions of the test material 122 and electrode material 124. The electrodes 120 are formed in a dielectric material 114 and are recessed below cantilever portions 108 and 110.

The material test structure 150 includes a base region 103 comprising a dielectric material 105 formed on a substrate material 101. A number of conductive elements can be formed in dielectric material 105 and can be used to couple other elements of the material test structure 150 to select device 128 and/or other circuitry associated therewith. Source/drain (SAD) regions 129-1 and 129-2 can be formed in substrate material 101 to couple conductive elements to select devices.

The material test structure can include a select device 128 formed on a substrate material 101. The select device 128 may be a field effect transistor, e.g., metal oxide semiconductor field effect transistor (MOSFET), a bipolar junction transistor (BJT) or a diode, among other types of select devices. The select device 128 is coupled to an electrode 120 of material test structure 150 via a conductive element 126. Conductive element 126 is a conductive plug coupling electrode 120 to conductive elements 123 and 125, which is coupled to a SID region 129-1 of select device 128. The conductive elements 123, 125, and 126 can be comprised of tungsten (W), titanium nitride (TiN), tantalum nitride (TaN), tantalum (Ta), and/or copper (Cu), for instance.

In the example illustrated in FIG. 1A, test material 122 is formed on and coupled to a number of electrodes 120. One of the number of electrodes 120 that is coupled to the test material is also coupled to a conductive plug 126. The electrode 120 that is coupled to the conductive plug 126 acts as a bottom electrode for the material test structure. The conductive plug 126 can be formed of a conductive material, such as tungsten (W), for example. The conductive plug 126 can couple the test material 122 and an electrode 120 to the select device 128. The test material structure can also include an electrode material 124 formed on the test material 122. The electrode material 124 can act as a top electrode for the material test structure. The test material structure includes electrode material 124, test material 122, which can represent an active material of a memory cell, and a bottom electrode 120, which is coupled to the select device 128 by conductive plug 126.

Operation of material test structure 150 can include providing voltage differences between electrode 120 and electrode material 124 formed on the test material 122 in order to determine various properties, e.g., physical and electrical characteristics, of the test material 122. The test material structure can be used to determine how the resistance of a test material changes when different voltages are applied to the material test structure 150, for instance.

FIG. 1B illustrates a cross-sectional view of a material test structure 160 having two levels of cantilever portions in accordance a number of embodiments of the present disclosure. The embodiment illustrated in FIG. 1B includes the elements described in association with FIG. 1A and also includes dielectric materials 112 formed on dielectric material 106 and dielectric material 130 formed on dielectric material 112. Cantilever portions 116 and 118 of the dielectric material 130 are formed by removing portions of dielectric material 112. The test material 122 and electrode material 124 can be formed on the cantilever portions 108, 110, 116, and 118 and on electrodes 120 of the material test structure. The portion of the test material 122 and the electrode material 124 formed on electrodes 120 is noncontiguous with the portion of the test material 122 and the electrode material 124 formed on cantilever portions 108, 110, 116, and 118, which provides for the test material 122 and electrode material 124 formed on the electrodes 120 to be separate from the test material and electrode material of adjacent material test structures, e.g., to avoid electrical shorts between adjacent test structures.

In a number of embodiments, material test structures can include multiple levels of cantilever portions. The addition of levels of cantilever portions can provide increased likelihood and/or certainty of physical and electrical isolation of a material test structure from other material test structures, for instance.

Figure 2A:
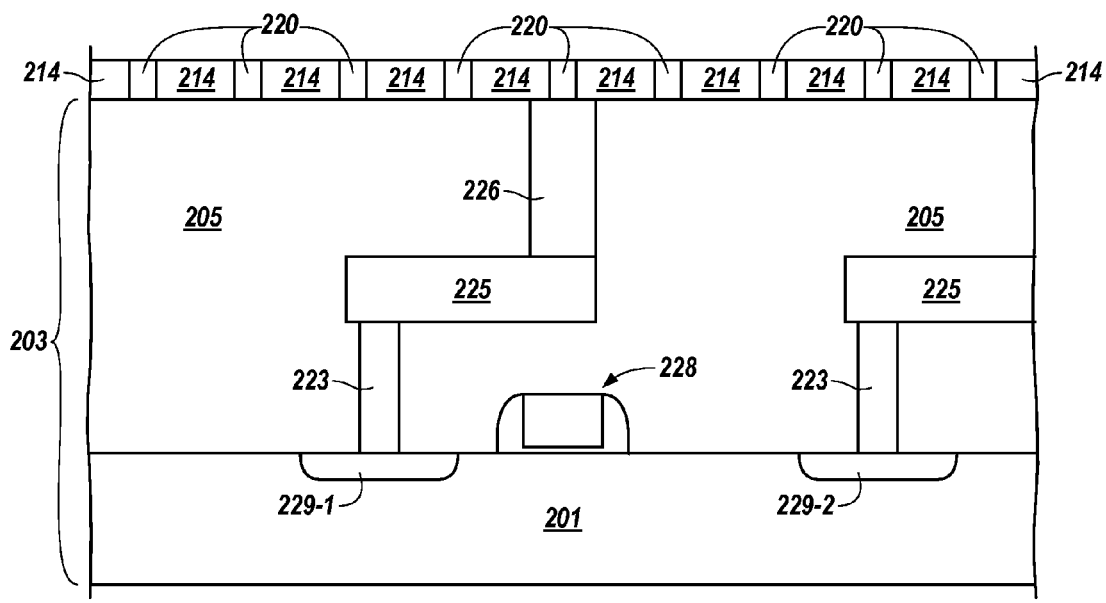
FIGS. 2A-2C illustrate various process stages associated with forming a material test structure in accordance with a number of embodiments of the present disclosure.
Figure 2B:
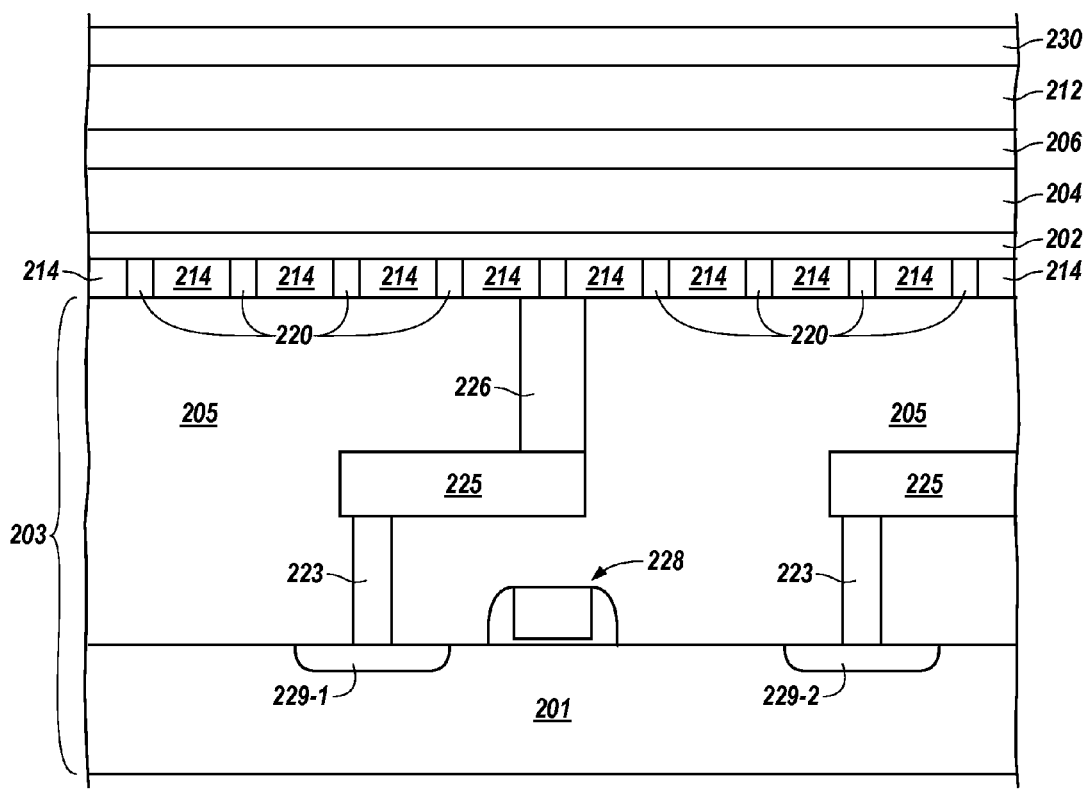
Figure 2C:
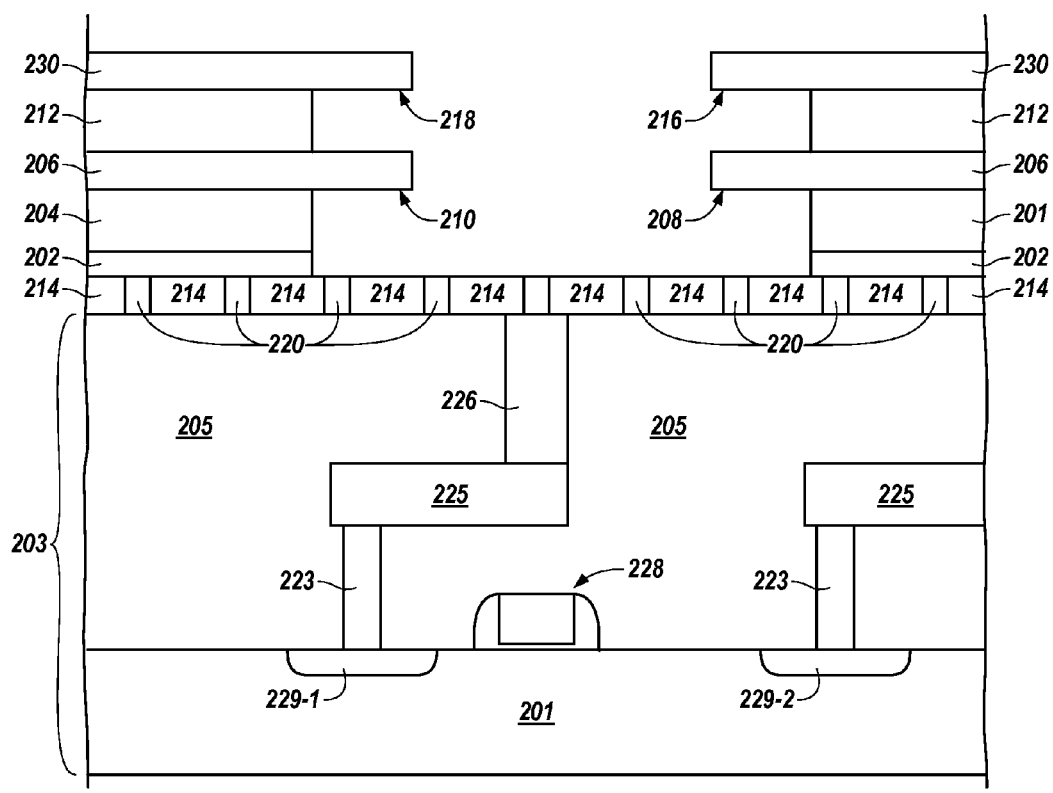

FIGS. 2A-2C illustrate various process stages associated with forming a material test structure in accordance with a number of embodiments of the present disclosure, e.g., a material test structure such as structure 160 shown in FIG. 1B. FIG. 2B includes a dielectric material 202 formed on a base region 203, e.g., a base region such as base region 103 shown in FIG. 1. The base region 203 includes a dielectric material 205, e.g., an oxide, formed on a substrate material 201, e.g., silicon. FIG. 2A illustrates a select device 228 formed in the base region 203. The select device 228 can be a field effect transistor, for instance. The base region 203 includes a number of conductive elements 223 and 225, which can represent a metallization level used to electrically couple portions of the material test structure to the select device 228, e.g., via source/drain regions 229-1 and 229-2, and/or to electrically couple portions of the material test structure to various other circuitry associated with testing material properties. Embodiments are not limited to the example base region 203 shown in FIG. 2A. For instance, the base region may comprise various dielectric materials and more or fewer conductive elements than those shown in FIG. 2A.

FIG. 2A illustrates a dielectric material 214 formed on dielectric material 205 and conductive plug 226. The dielectric material 214 can be a nitride, such as silicon nitride ($Si_3N_4$), for example. A number of electrodes 220, which can function as a bottom electrode for the test material structure, are formed in the dielectric material 214. The electrodes 220 can comprise materials such as copper, platinum, tungsten, silver, titanium nitride (TiN), tantalum nitride (TaN), and/or carbon, among various other conductive materials and/or combinations thereof. The electrodes 220 can be formed using a subtractive approach or a damascene approach, for instance. The electrodes 220 can be formed such that only one of the electrodes 220 is coupled to conductive plug 226. A portion of the dielectric material 214 and the electrodes 220 can be removed, e.g., via a CMP process.

FIG. 2B illustrates a process stage subsequent to that shown in FIG. 2A. FIG. 2B illustrates a dielectric materials 202, 204, 206, 212, and 230 formed on the dielectric material 214 and the electrodes 220. In a number of embodiments, a planarization process, e.g., CMP, can be performed on an upper surface of dielectric material 214 and electrodes 220 prior to formation of dielectric 202 thereon. In this example, a dielectric material 204 is formed on the dielectric material 202, a dielectric material 206 is formed on the dielectric material 204, a dielectric material 212 is formed on the dielectric material 206, and a dielectric material 230 is formed on the dielectric material 212. The dielectric materials 202, 206, and 230 can be a nitride, such as silicon nitride ($Si_3N_4$), for example. The dielectric materials 204 and 212 can be an oxide, such as silicon oxide ($SiO_2$), for example.

FIG. 2C illustrates a process stage subsequent to that shown in FIG. 2B. As shown in FIG. 2C, portions of the dielectric materials 230, 212, 206, 204, and 202 can be removed. The portions of the dielectric materials 230, 212, 206, and 204 can be removed via a selective etch process that can include dry etching and/or wet etching. Dielectric material 202 can act as a protective layer that protects dielectric material 214 and electrodes 220 from the selective etch process that removes portions of dielectric materials 230, 212, 206, and 204. The removal of the portions of the dielectric materials 230, 212, 206, and 204 form cantilever portions 208, 210, 216, and 218 of the test material structure. The selective etch process can form lateral recessions in dielectric materials 204 and 212, leaving portions of dielectric materials 206 and 230 extending laterally from dielectric materials 204 and 212. The cantilever portions 208, 210, 216, and 218 are formed in dielectric materials 206 and 230 due the lateral recessions formed in dielectric materials 204 and 212. The lateral recessions in dielectric materials 204 and 212 can be formed in dielectric materials 204 and 212 because the etch rate of the dielectric materials 204 and 212, which can be an oxide, for example, is greater than the etch rate of dielectric materials 206 and 230, which can be a nitride, for example. Portions of dielectric materials 202 can be removed via a dry and/or wet etch process to expose dielectric material 214 and electrodes 220. Also, the removal the portions of the dielectric materials 230, 214, 212, 206, and 204 can also form and isolate the test material structure from adjacent test material structures, e.g., when forming an array of test material structures.

As shown in FIG. 1B, a test material 122 and an electrode material 124, which can act as the top electrode for the material test structure, can be subsequently formed on the structure shown in FIG. 2C. The test material 122 and electrode material 124 can be formed using a non-conformal process, such as physical vapor deposition (PVD). The test material 122 and electrode material 124 can be formed on cantilever portions 108 and 112 of dielectric material 106, the cantilever portions 116 and 118 of dielectric material 114, the dielectric material 114, and the electrodes 120.

In a number of embodiments, forming the test material 122 and the electrode material 124 on cantilever portions 108, 112, 116, and 118 using a non-conformal process can create noncontiguous portions of the test material 122 and electrode material 124 because the non-conformal process will not form the test material 122 and electrode material 124 on the sidewalls of the dielectric materials 102, 104, and 112. The noncontiguous portions of the test material and electrode material 124 are isolated from other portions of the test material and electrode material that may be associated with an adjacent material test structure.

Figure 3A:
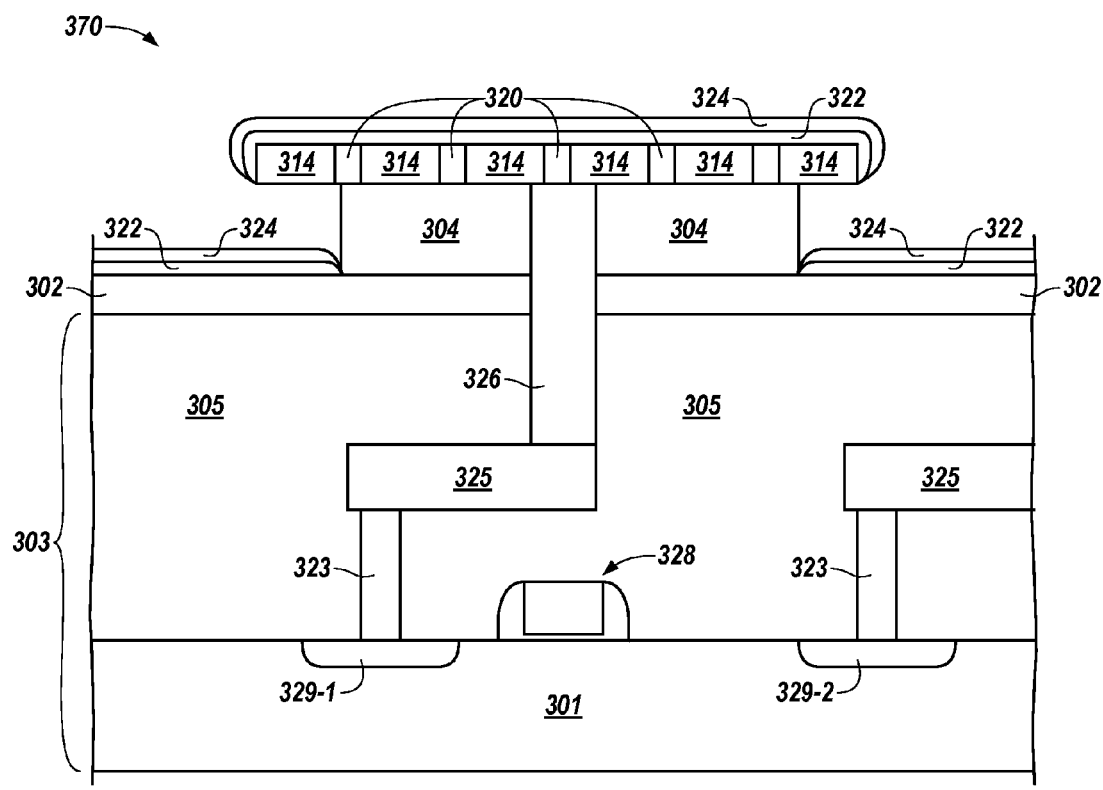
FIGS. 3A-3B illustrate cross-sectional views of material test structures in accordance a number of embodiments of the present disclosure.
Figure 3B:
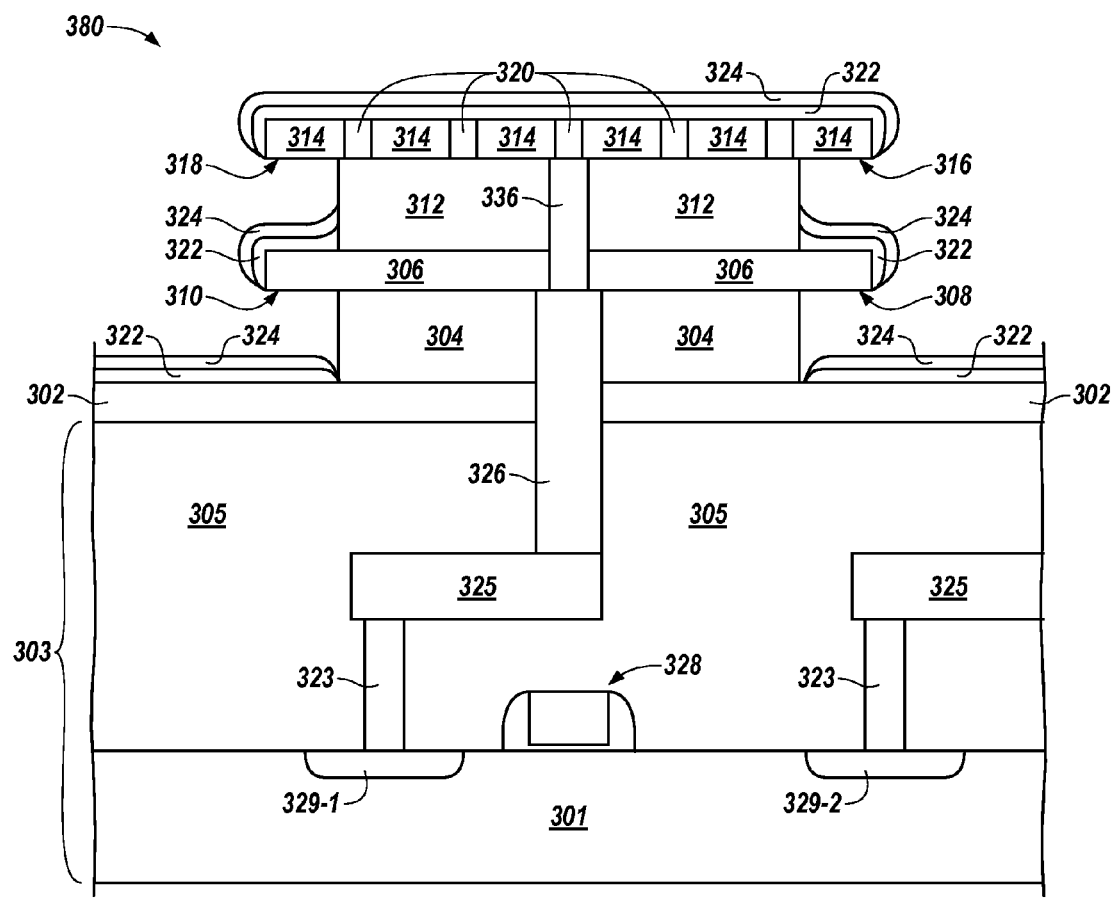

FIGS. 3A-3B illustrate cross-sectional views of material test structures in accordance a number of embodiments of the present disclosure. FIG. 3A illustrates a cross-sectional view of a material test structure 370 having one level of cantilever portions in accordance a number of embodiments of the present disclosure. The material test structure 370 includes a test material 322 whose properties, e.g., physical and/or electrical characteristics, can be tested and observed using the material test structure of the present disclosure. The material test structure 370 can be used to simulate operation of a memory cell during the testing of different test materials. The test material 322 can be, for example, materials such as test material 122 described above.

The material test structure illustrated in FIG. 3B includes portions of the test material 322 and the electrode material 324 formed on cantilever portions 308, 310, 316, and 318. The electrode material 324 can act as a top electrode for the material test structure. The portion of the test material 322 and the electrode material 324 formed on cantilever portions 316 and 318 and on electrodes 320 is noncontiguous with the portion of the test material 322 and the electrode material 324 formed on cantilever portions 308 and 310, which allows the test material 322 and electrode material 324 formed on the electrodes 320 to be separate from the test material and electrode material of adjacent material test structures to avoid electrical shorts between adjacent test structures. The test material 322 and electrode material 324 can be formed using a non-conformal deposition process to form the noncontiguous portions of the test material 322 and electrode material 324. The electrodes 320 are formed in a dielectric material 314, from which cantilever portions 316 and 318 are formed. In a number of embodiments, an etch process that removes portions of 320, 314, 312, 310, 306, and 304 to form cantilever portions 308, 310, 316, 318 can be performed subsequent to planarizing the surface of the electrodes 320 and such that the electrodes 320 that interface with test material 322 are not affected by the etch process. In a number of embodiments, electrodes 320 can be formed above and after cantilever portions 308 and 310, allowing the test material 322 and electrode material 324 to be formed on the electrodes 320 without having process steps, such as an etch process, affect the surface of the electrodes 320 that interfaces with the test material 322. In a number of embodiments, the test material 322 can be formed directly after planarizing the surface of the electrodes 320.

The material test structure 370 includes a base region 303 comprising a dielectric material 305 formed on a substrate material 301. A number of conductive elements can be formed in dielectric material 305 and can be used to couple other elements of the material test structure 370 to select device 328 and/or other circuitry associated therewith.

The material test structure can include a select device 328 formed on a substrate material 301. The select device 328 may be a field effect transistor, e.g., metal oxide semiconductor field effect transistor (MOSFET), a bipolar junction transistor (BJT) or a diode, among other types of select devices. The select device 328 is coupled to an electrode 320 of material test structure 370 via a number of conductive elements 326 and 336. Conductive elements 323, 325, 326, and 336 are conductive plugs coupling electrode 320 to a metallization level 325, which is coupled to a SID region 329-1 of select device 328. The conductive elements 326 and 336 can be comprised of tungsten (W), titanium nitride (TiN), tantalum nitride (TaN), tantalum (Ta), and/or copper (Cu), for instance.

In the example illustrated in FIG. 3A, test material 322 is formed on and coupled to a number of electrodes 320. One of the number of electrodes 320 that is coupled to the test material is also coupled to a conductive plug 326. The electrode 320 that is coupled to the conductive plug 326 acts as a bottom electrode for the material test structure. The conductive plug 326 can be formed of a conductive material, such as tungsten (W), for example. The conductive plug 326 can couple the test material 322 and an electrode 320 to the select device 328. The test material structure can also include an electrode material 324 formed on the test material 322. The electrode material 324 can act as a top electrode for the material test structure. The test material structure includes electrode material 324, test material 322, which can represent an active material of a memory cell, and a bottom electrode 320, which is coupled to the select device 328 by conductive plug 326.

Operation of material test structure 370 can include providing voltage differences between electrode 320 and electrode material 324 formed on the test material 322 in order to determine various properties, e.g., physical and electrical characteristics, of the test material 322. The test material structure can be used to determine how the resistance of a test material changes when different voltages are applied to the material test structure 370.

FIG. 3B illustrates a cross-sectional view of a material test structure 380 having two levels of cantilever portions in accordance a number of embodiments of the present disclosure. The embodiment illustrated in FIG. 3B includes the elements described in association with FIG. 3A and also includes dielectric materials 306 and 312 formed on dielectric material 304 and dielectric material 314 and electrodes 320 formed on dielectric material 312. In FIG. 3B, conductive element 336 is formed in dielectric materials 306 and 312 to couple an electrode 320 to conductive element 326. Cantilever portions 316 and 318 of the dielectric material 330 are formed by removing portions of dielectric material 312. The test material 322 and electrode material 324 can be formed on the cantilever portions 308, 310, 316, and 318 and on electrodes 320 of the material test structure. The portion of the test material 322 and the electrode material 324 formed on electrodes 320 is noncontiguous with the portion of the test material 322 and the electrode material 324 formed on cantilever portions 308, 310, 316, and 318, which provides for the test material 322 and electrode material 324 formed on the electrodes 320 to be separate from the test material and electrode material of adjacent material test structures to avoid electrical shorts between adjacent test structures.

In a number of embodiments, material test structures can include a number of levels of cantilever portions. The addition of levels of cantilever portions can provide increased likelihood and/or certainty of physical and electrical isolation of a material test structure from other material test structures. Also, the addition of levels of cantilever portions increases the aspect ratio of the conductive elements that are used to couple an electrode to a select device.

Figure 4A:
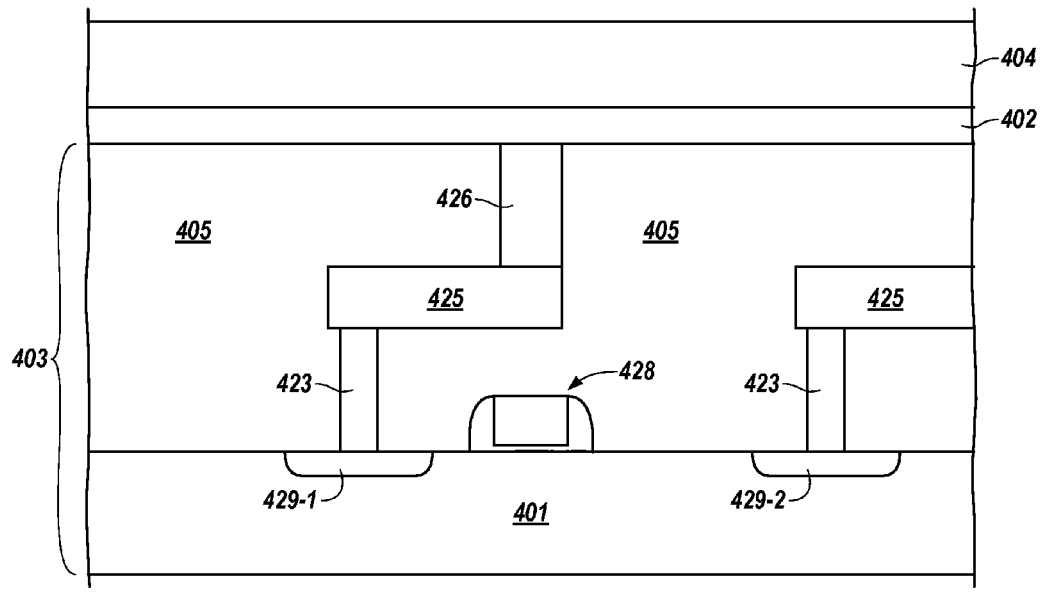
FIGS. 4A-4F illustrate various process stages associated with forming a material test structure in accordance with a number of embodiments of the present disclosure.

FIGS. 4A-4F illustrate various process stages associated with forming a material test structure in accordance with a number of embodiments of the present disclosure, e.g., a material test structure such as structure 380 shown in FIG. 3B, having two levels of cantilever portions. FIG. 4A includes a dielectric material 402 formed on a base region 403, e.g., a base region such as base region 103 shown in FIG. 1. The base region 403 includes a dielectric material 405, e.g., an oxide, formed on a substrate material 401, e.g., silicon. FIG. 4A illustrates a select device 428 formed in the base region 403. The select device 428 can be a field effect transistor, for instance. The base region 403 includes a number of conductive elements 423 and 425, which can represent a metallization level used to electrically couple portions of the material test structure to the select device 428, e.g., via source/drain regions 429-1 and 429-2, and/or to electrically couple portions of the material test structure to various other circuitry associated with testing material properties. Embodiments are not limited to the example base region 403 shown in FIG. 4A. For instance, the base region may comprise various dielectric materials and more or fewer conductive elements than those shown in FIG. 4A.

The dielectric material 402 formed on base region 403 can be a nitride, such as silicon nitride ($Si_3N_4$), for example. In this example, a dielectric material 404 is formed on the dielectric material 402. The dielectric material 404 can be an oxide, such as silicon oxide ($SiO_2$), for example.

Figure 4B:
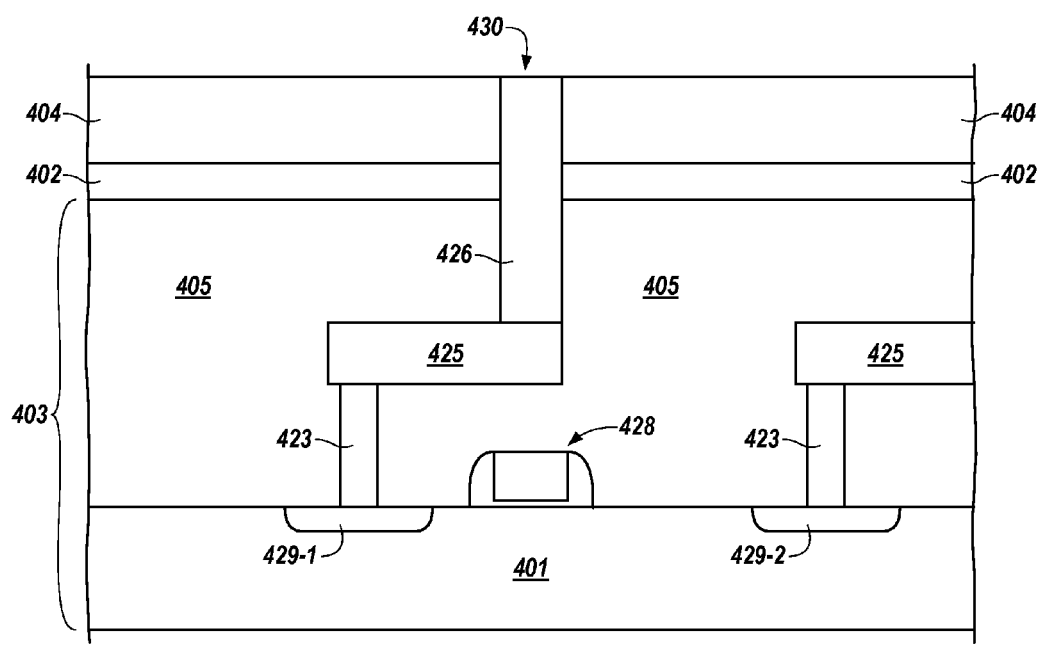
Figure 4C:
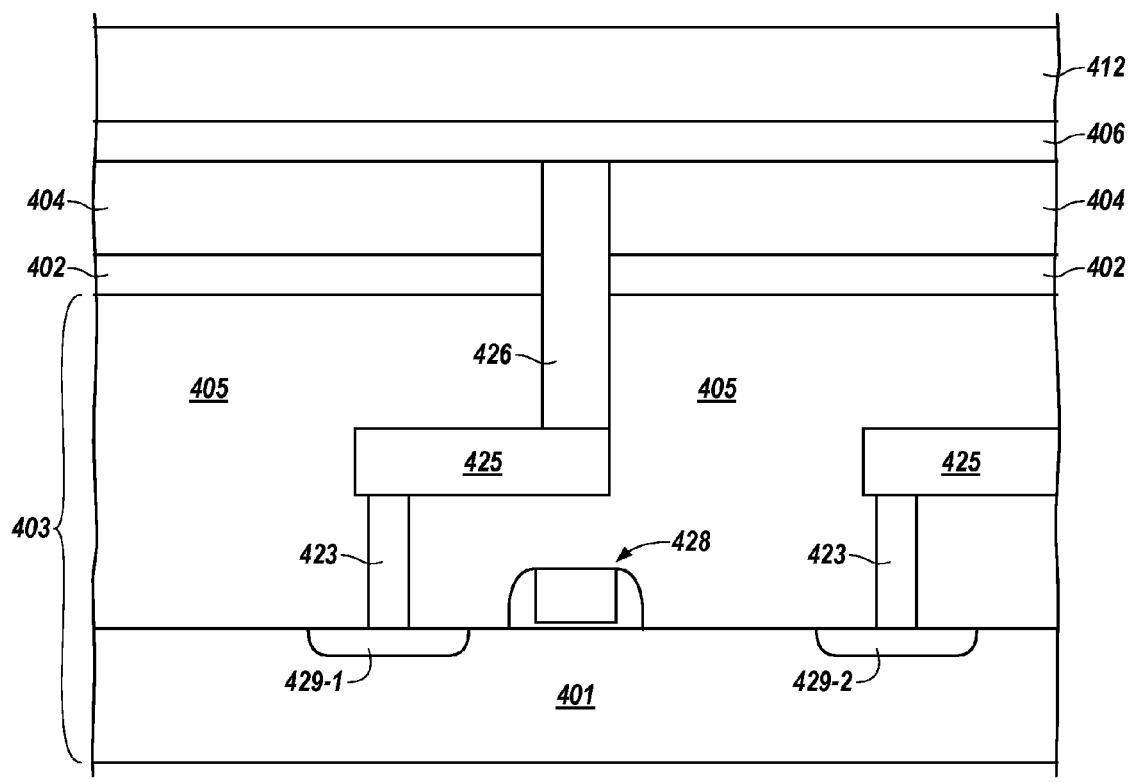

FIG. 4B illustrates a process stage subsequent to that shown in FIG. 4A. FIG. 4B illustrates an opening 430 formed by removing portions of the dielectric materials 402, 404, and 405, e.g., via a masking and etching process. As an example, the opening 430 can be a circular via; however, embodiments are not so limited. As shown in FIG. 4C, a conductive material, such as tungsten, can be formed in the opening 430 to form a conductive plug 426. As described further below, the conductive plug 426 can be used to couple an electrode of the material test structure to select device 428.

FIG. 4C also illustrates a dielectric material 406 formed on the dielectric material 404 and the conductive plug 426. The dielectric material 406 can be a nitride, such as silicon nitride ($Si_3N_4$), for example. In a number of embodiments, a planarization process, e.g., CMP, can be performed on an upper surface of materials 404 and 426 prior to formation of dielectric 406 thereon. In this example, a dielectric material 412 is formed on the dielectric material 406. The dielectric material 412 can be an oxide, such as silicon oxide ($SiO_2$), for example.

Figure 4D:
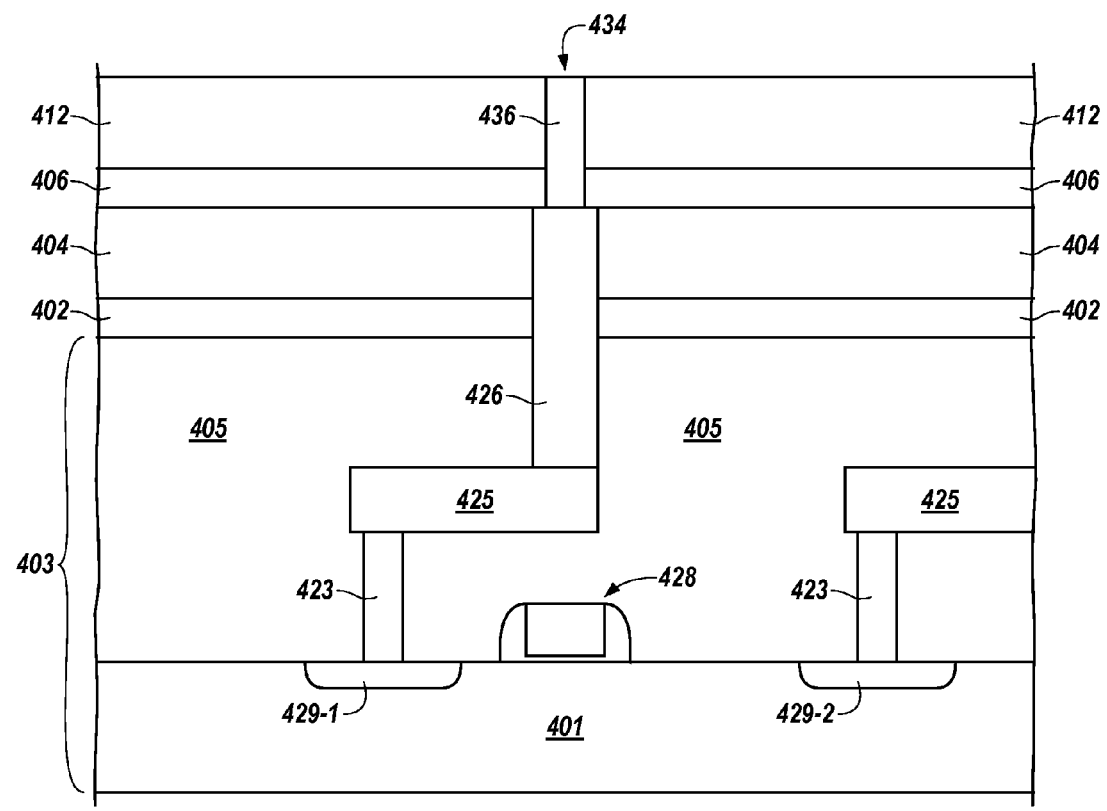

FIG. 4D illustrates a process stage subsequent to that shown in FIG. 4C. FIG. 4D illustrates a conductive plug 436 formed in an opening 434. The opening 434 can be formed by removing portions of the dielectric materials 406 and 412, e.g., via a masking and etching process. As an example, the opening 434 can be a circular via; however, embodiments are not so limited. The etch process used to remove portions of the dielectric materials 406 and 412 can end on the conductive plug 426 such that an upper surface of the conductive plug 426 is exposed. As such, the conductive plug 436 can be formed on the conductive plug 426. The conductive plug 436 can be formed of a conductive material, such as tungsten, for example. Although embodiments are not so limited, the conductive plugs 436 and 426 can be formed of the same material (s).

In the example shown in FIGS. 4A-4D, two separate conductive plugs 426 and 436 are formed to create a conductive path through materials 412, 406, 404, 402, and 405. However, embodiments are not so limited. For instance, in a number of embodiments, a single opening can be formed through the stack of materials 412, 406, 404, 402, and 405, and a single conductive plug can be formed therein. However, a single via formed through the stack of materials 412, 406, 404, 402, and 405 may have an aspect ratio that is too high to provide for an effective conductive material fill. Forming separate conductive plugs can ensure a proper contact between the plugs, e.g., 436 and 426, and the conductive element beneath, e.g., conductive element 425. As such, the conductive plug 436 has a smaller critical dimension, e.g., diameter, than the critical dimension of the conductive plug 426.

Figure 4E:
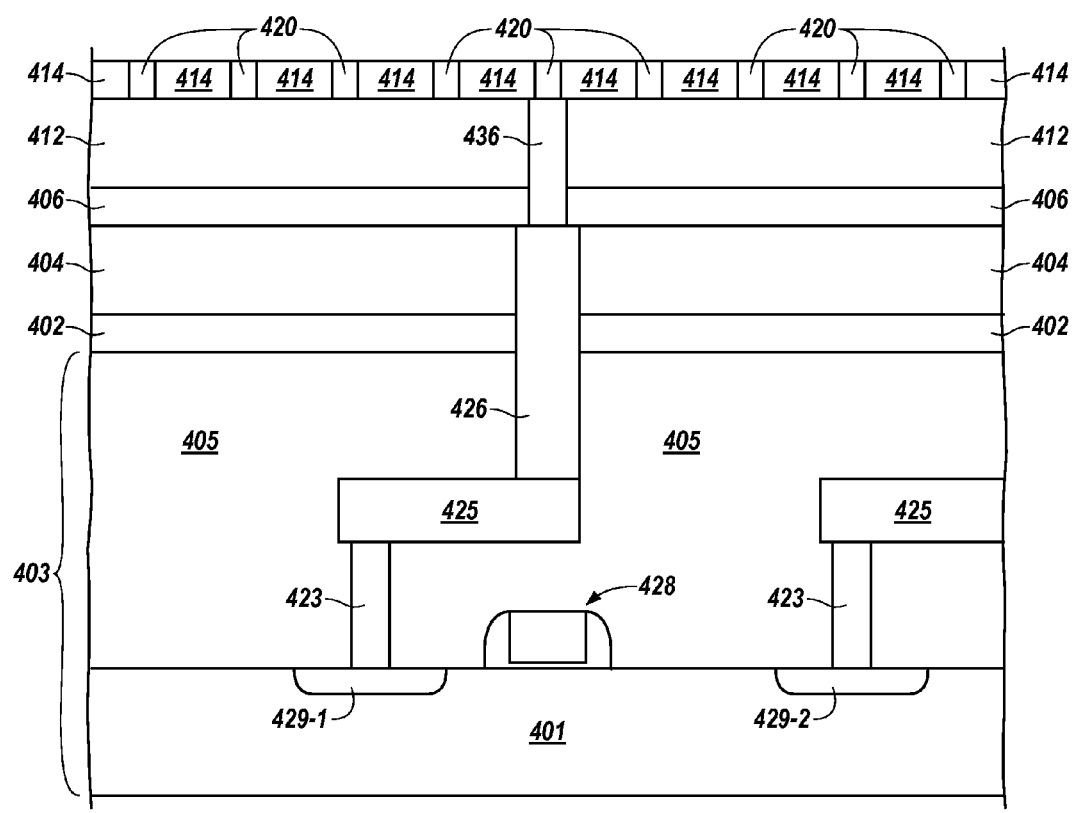

FIG. 4E illustrates a process stage subsequent to that shown in FIG. 4D. FIG. 4E illustrates a dielectric material 414 formed on dielectric material 412 and conductive plug 436. The dielectric material 414 can be a nitride, such as silicon nitride ($Si_3N_4$), for example. A number of electrodes 420, which can function as a bottom electrode for the test material structure, are formed in the dielectric material 414. The electrodes 420 can comprise materials such as copper, platinum, tungsten, silver, titanium nitride (TiN), tantalum nitride (TaN), and/or carbon, among various other conductive materials and/or combinations thereof. The electrodes 420 can be formed using a subtractive approach or a damascene approach, for instance. The electrodes 420 can be formed such that only one of the electrodes 420 is coupled to conductive plug 436. A portion of the dielectric material 414 and the electrodes 420 can be removed, e.g., via a CMP process. The CMP process can form a contact surface on which a test material can be formed.

Figure 4F:
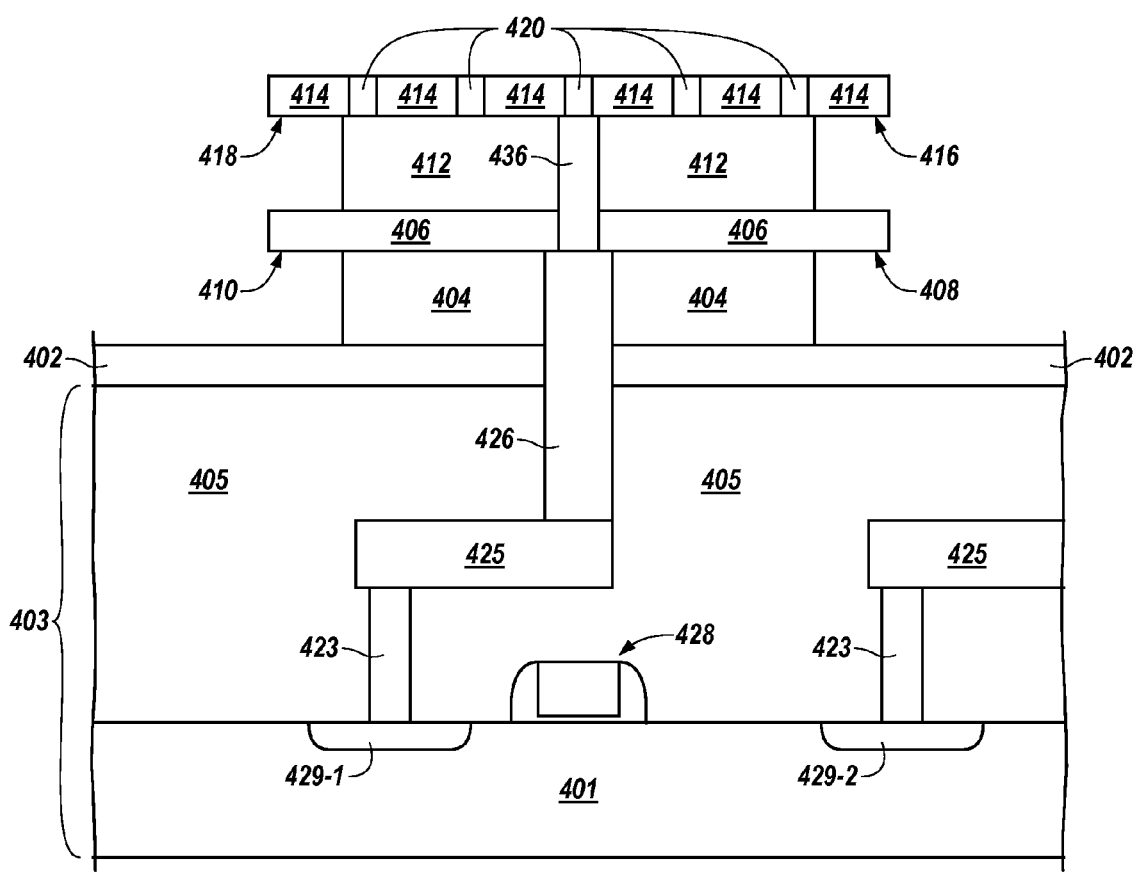

FIG. 4F illustrates a process stage subsequent to that shown in FIG. 4E. As shown in FIG. 4F, portions of the dielectric materials 414, 412, 406, and 404 can be removed. The portions of the dielectric materials 414, 412, 406, and 404 can be removed via a selective etch process that can include dry etching and/or wet etching. The removal of the portions of the dielectric materials 414, 412, 406, and 404 can expose dielectric material 402 and form cantilever portions 408, 410, 416, and 418 of the test material structure. The selective etch process can form lateral recessions in dielectric materials 404 and 412, leaving portions of dielectric materials 406 and 414 extending laterally from dielectric materials 404 and 412. The cantilever portions 408, 410, 416, and 418 are formed in dielectric materials 406 and 414 due the lateral recessions formed in dielectric materials 404 and 412. The lateral recessions in dielectric materials 404 and 412 can be formed in dielectric materials 404 and 412 because the etch rate of the dielectric materials 404 and 412, which can be an oxide, for example, is greater than the etch rate of dielectric materials 406 and 414, which can be a nitride, for example. Also, the removal the portions of the dielectric materials 414, 412, 406, and 404 can also form and isolate the test material structure from adjacent test material structures, e.g., when forming an array of test material structures.

As shown in FIG. 3B, a test material 322 and an electrode material 324, which can act as the top electrode for the material test structure, can be subsequently formed on the structure shown in FIG. 4F. The test material 322 and electrode material 324 can be formed using a non-conformal process, such as physical vapor deposition (PVD). The test material 322 and electrode material 324 can be formed on cantilever portions 308 and 312 of dielectric material 306, the cantilever portions 316 and 318 of dielectric material 314, the dielectric material 302, the dielectric material 314, and the electrodes 320. The test material 322 can be formed on the dielectric material 314 and the electrodes 320 such that the electrodes 320 are not affected by further processing on the material test structure after the formation and planarization of the electrodes 320. The electrodes 320 are formed in and/or above the cantilever portions 308, 310, 316 and 318 allowing the test material 322 to be formed on the electrodes 320 without having process steps, such as etching, affect the surface of the electrodes 320 that interface with the test material 322. In a number of embodiments, an etch process that removes portions of 320, 314, 312, 310, 306, and 304 to form cantilever portions 308, 310, 316, 318 can be performed subsequent to planarizing the surface of the electrodes 320 and such that the electrodes 320 that interface with test material 322 are not affected by the etch process. In a number of embodiments, electrodes 320 can be formed above and after cantilever portions 308 and 310, allowing the test material 322 and electrode material 324 to be formed on the electrodes 320 without having process steps, such as an etch process, affect the surface of the electrodes 320 that interfaces with the test material 322. In a number of embodiments, the test material 322 can be formed directly after planarizing the surface of the electrodes.

In a number of embodiments, forming the test material 322 and the electrode material 324 on cantilever portions 308, 312, 316, and 318 using a non-conformal process can create noncontiguous portions of the test material 322 and electrode material 324 because the non-conformal process will not form the test material 322 and electrode material 324 on the sidewalls of the dielectric material 304 and 312. The noncontiguous portions of the test material and electrode material 324 are isolated from other portions of the test material and electrode material that may be associated with an adjacent material test structure.

As will be appreciated, elements shown in the various embodiments herein can be added, exchanged, and/or eliminated so as to provide a number of additional embodiments of the present disclosure. In addition, the proportion and the relative scale of the elements provided in the figures are intended to illustrate various embodiments of the present invention and are not to be used in a limiting sense.

Although specific embodiments have been illustrated and described herein, those of ordinary skill in the art will appreciate that an arrangement calculated to achieve the same results can be substituted for the specific embodiments shown. This disclosure is intended to cover adaptations or variations of various embodiments of the present disclosure.

It is to be understood that the above description has been made in an illustrative fashion, and not a restrictive one. Combination of the above embodiments, and other embodiments not specifically described herein will be apparent to those of skill in the art upon reviewing the above description. The scope of the various embodiments of the present disclosure includes other applications in which the above structures and methods are used. Therefore, the scope of various embodiments of the present disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the disclosed embodiments of the present disclosure have to use more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method of forming a material test structure, the method comprising:
    forming a number of electrode portions in a first dielectric material;
    forming a second dielectric material on the first dielectric material, wherein the second dielectric material includes a first cantilever portion and a second cantilever portion; and
    forming a first portion of a test material on the number of electrode portions, a second portion of the test material on the first dielectric material, and a third portion of the test material on the second dielectric material, wherein the first, second, and third portions of the test material are noncontiguous.

2. The method claim 1, wherein the method includes planarizing the number of electrode portions and the first dielectric material prior to forming the test material.

3. The method claim 2, wherein planarizing the number of electrode portions and the first dielectric material includes performing a chemical mechanical planarization (CMP) process.

4. The method of claim 2, wherein the method includes forming a conductive plug that couples one of the number of electrode portions and the test material to a select device.

5. The method claim 1, wherein method includes forming the test material on the number of electrode portions, the first dielectric material, and the second dielectric material via physical vapor deposition (PVD).

6. The method claim 1, wherein forming the test material includes forming a resistance variable material on the number of electrode portions, the first dielectric material, and the second dielectric material.

7. The method claim 1, wherein the method includes forming an electrode material on the test material.

8. A method of forming a number of material test structures, the method comprising:
    forming a number of electrode portions in one of a number of dielectric materials and planarizing a surface of the number of electrode portions;
    forming a number of openings by removing a number of portions of the number of dielectric materials, wherein forming the number of openings separates the number of material test structures from each other and wherein removing the number of portions of the number of dielectric materials forms a number of cantilever portions in the number of dielectric materials; and
    forming a number of noncontiguous test material portions on the number of cantilever portions and the number of electrode portions; and
    forming an electrode material on the test material.

9. The method claim 8, wherein forming the test material includes forming a number of portions of the test material on each material test structure that are noncontiguous to the test material of an adjacent material test structure.

10. The method claim 8, wherein removing the number of portions of the dielectric materials includes performing a dry etch process and a wet etch process.

11. The method claim 8, wherein removing the number of portions of the dielectric materials includes forming a number of lateral recessions in the dielectric materials.

12. The method claim 8, wherein the method includes forming the test material on the number of cantilever portions and the number of electrode portions via physical vapor deposition (PVD).

13. The method claim 8, wherein the method includes forming the test material on the number of cantilever portions and the number of electrode portions without further processing of the number of electrode portions after planarization of the surface of the number of electrode portions.

14. A method of forming a material test structure, the method comprising:
    forming a conductive plug in a number of dielectric materials, the plug coupling an electrode to a select device formed in a substrate;
    performing a selective etch to remove a number of portions of the number of dielectric materials such that a number of cantilever portions are formed;
    forming a number of noncontiguous test material portions on the number of cantilever portions and the electrode.

15. The method claim 14, wherein the method includes planarizing a surface of the electrode.

16. The method claim 14, wherein the method includes forming the test material via a non-conformal deposition process.

17. The method claim 14, wherein the number of noncontiguous test material portions are physically and electrically isolated from each other.

* * * * *

UNITED STATES PATENT AND TRADEMARK OFFICE
CERTIFICATE OF CORRECTION

PATENT NO. : 8,945,403 B2  
APPLICATION NO. : 13/458048  
DATED : February 3, 2015  
INVENTOR(S) : Fabio Pellizzer et al.

Page 1 of 1

It is certified that error appears in the above-identified patent and that said Letters Patent is hereby corrected as shown below:

In the Claims

In column 10, line 65, in Claim 2, delete "method claim" and insert -- method of claim --, therefor.

In column 11, line 1, in Claim 3, delete "method claim" and insert -- method of claim --, therefor.

In column 11, line 8, in Claim 5, delete "method claim" and insert -- method of claim --, therefor.

In column 11, line 12, in Claim 6, delete "method claim" and insert -- method of claim --, therefor.

In column 11, line 17, in Claim 7, delete "method claim" and insert -- method of claim --, therefor.

In column 11, line 35, in Claim 9, delete "method claim" and insert -- method of claim --, therefor.

In column 12, line 3, in Claim 10, delete "method claim" and insert -- method of claim --, therefor.

In column 12, line 6, in Claim 11, delete "method claim" and insert -- method of claim --, therefor.

In column 12, line 9, in Claim 12, delete "method claim" and insert -- method of claim --, therefor.

In column 12, line 13, in Claim 13, delete "method claim" and insert -- method of claim --, therefor. In column 12, line 27, in Claim 15, delete "method claim" and insert -- method of claim --, therefor. In column 12, line 29, in Claim 16, delete "method claim" and insert -- method of claim --, therefor. In column 12, line 32, in Claim 17, delete "method claim" and insert -- method of claim --, therefor.

Signed and Sealed this  
Fifth Day of May, 2015

Michelle K. Lee  
*Director of the United States Patent and Trademark Office*